United States Patent [19]

Lu

[11] Patent Number: 5,571,095
[45] Date of Patent: Nov. 5, 1996

[54] DISPOSABLE URINE BAG FOR FEMALES

[75] Inventor: Ke-Way Lu, Taipei, Taiwan

[73] Assignee: Flying Point Enterprise, Co., Taipei City, Taiwan

[21] Appl. No.: 520,819

[22] Filed: Aug. 30, 1995

[51] Int. Cl.$^6$ .................. A61F 5/44; A61B 5/00
[52] U.S. Cl. .......... 604/329; 604/330; 128/761
[58] Field of Search .................. 604/329, 330, 604/332, 339, 342; 128/761; 4/144.1–144.3

[56] References Cited

U.S. PATENT DOCUMENTS 3,736,934  6/1973  Hennessy ................... 604/342
5,422,076  6/1995  Jones ....................... 128/761

Primary Examiner—John G. Weiss
Assistant Examiner—David J. Cho
Attorney, Agent, or Firm—Ladas & Parry

[57] ABSTRACT

A disposable urine bag for females, including a bracket having an open bearing frame at one end for fitting around the vulva and a flat handle at an opposite end for carrying by hand, a polybag fastened to the open bearing frame for collecting urine, and a packing member fitted into an endless mounting groove on the open bearing frame to hold down the polybag.

3 Claims, 3 Drawing Sheets

DISPOSABLE URINE BAG FOR FEMALES

BACKGROUND OF THE INVENTION

The present invention relates to disposable urine bags, and relates more particularly to such a disposable urine bag specifically designed for females.

Because of physiological differences, females must sit with the legs drawn up closely beneath the body when discharging urine. If a female stands up while discharging urine, the clothes and other part of the body will be contaminated by urine. In some emergency cases, it is more difficult to a female to fine a place for passing urine. Furthermore, to some aged or disabled persons, it is not easy to get a place nearby for passing urine when in a hurry.

SUMMARY OF THE INVENTION

The present invention has been accomplished under the circumstances in view. It is one object of the present invention to provide a disposable urine bag which is specifically designed for females. It is another object of the present invention to provide a disposable urine bag for females which can be carried by hand to collect urine at a standing position.

According to the preferred embodiment of the present invention, the disposable urine bag comprises a bracket for carrying a polybag for collecting urine, a polybag for collecting urine, and a packing member fastened to the bracket to hold down the polybag. The bracket has a flat handle at one end for carrying by hand the handle having two recesses at opposing sides and each recess having a coarse surface to aid in gripping the bracket, and a bearing frame at an opposite end for fitting around the vulva. The bearing frame has an endless mounting groove and a plurality of pointed blocks at the endless mounting groove. The packing member is fitted into the endless mounting groove on the bearing frame to fix the water-proof bag in place, having a plurality of notches, which engage with the pointed blocks of the bearing frame the polybag has a plurality of splits around the border of its opening; these splits allow the border of the bag opening to be easily turned inside out to ease the polybag's fastening with the mounting groove of the bearing frame.

DETAILED DESCRIPTION OF THE PREFERRED EMBODIMENT

Figures 1, 1A:
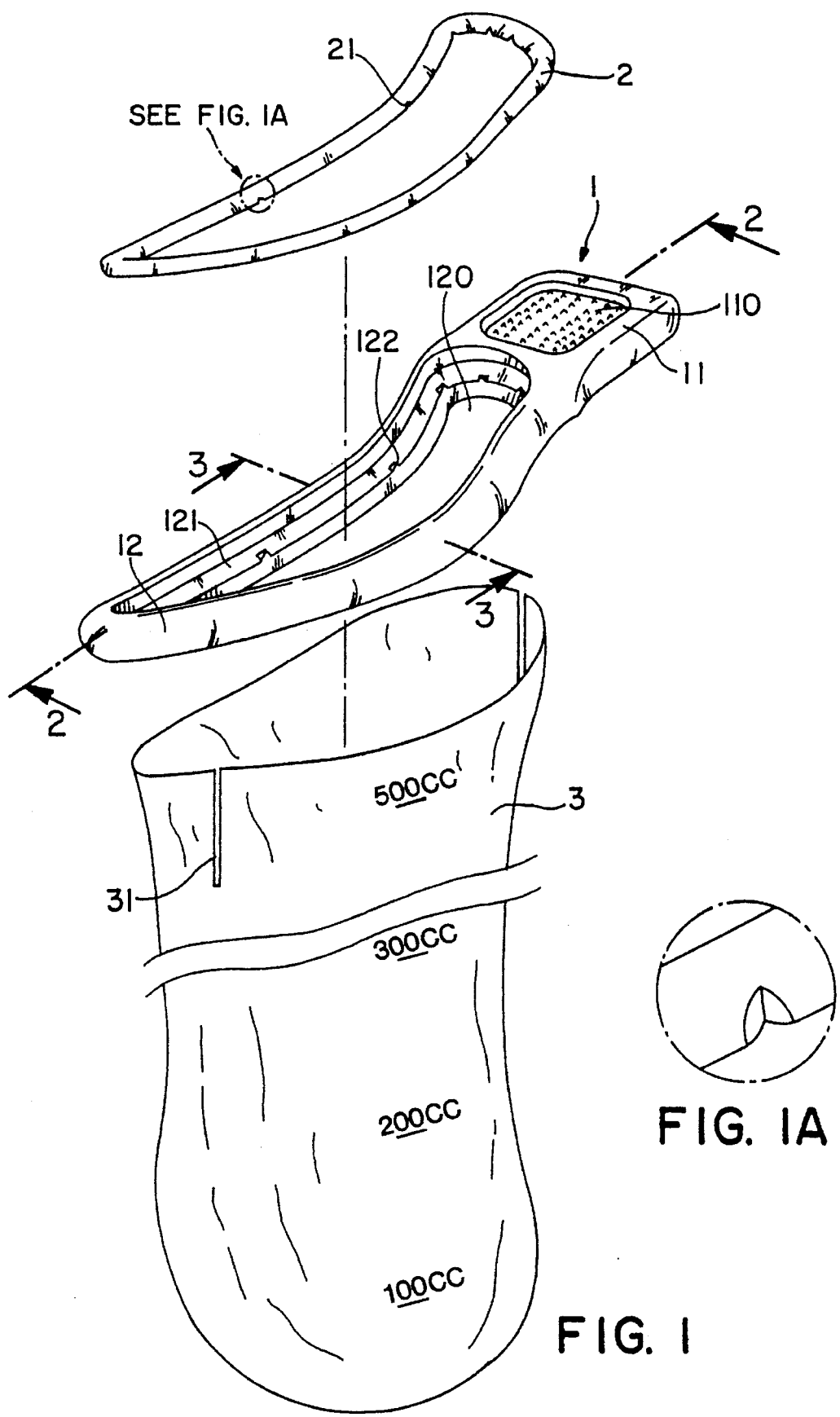
FIG. 1 is an exploded view of a disposable urine bag according to the present invention.
Figure 2:
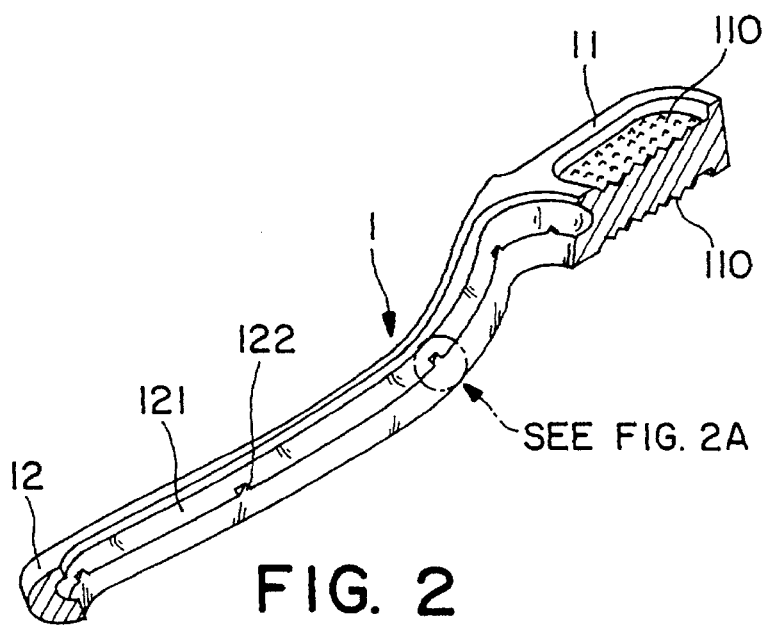
FIG. 2 is a cutaway view taken along line A—A of the bracket shown in FIG. 1.
Figure 2A:
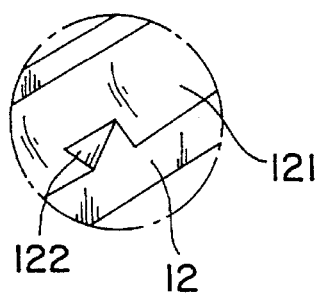
Figure 3:
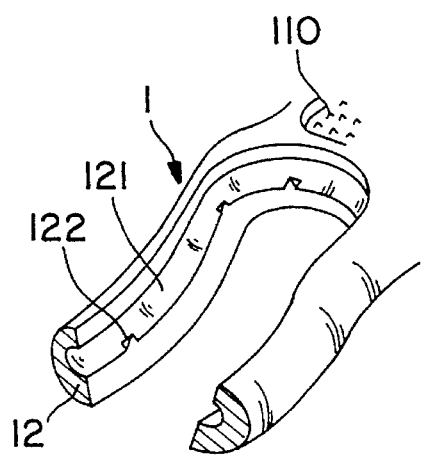
FIG. 3 is a cutaway view taken along line B—B of the bracket shown in FIG. 1.

Referring to FIGS. 1, 2, and 3, a disposable urine bag for females according to the present invention is generally comprised of a bracket 1, a packing rubber 2, and a polybag 3. The bracket 1 comprises a flat handle 11 at one end, and an open bearing frame 12 at an opposite end for fitting around the vulva. The flat handle 11 has two coarsely surfaced recesses 110 at two opposite sides for holding by hand positively. The open bearing frame 12 comprises an endless mounting groove 121 at the top side around the center opening 120 thereof, and a plurality of triangular blocks 122 at the mounting groove 121. The packing rubber 2 fits the endless mounting groove 121, having a plurality of notches 21 corresponding to the triangular blocks 122 of the open bearing frame 12. The polybag 3 is for collecting urine, having a plurality of splits 31 around the opening. The size of the polybag 3 is suitable for carrying about 500 cc of urine (the maximum amount of urine one discharges at one time is about 450 cc).

Figure 4:
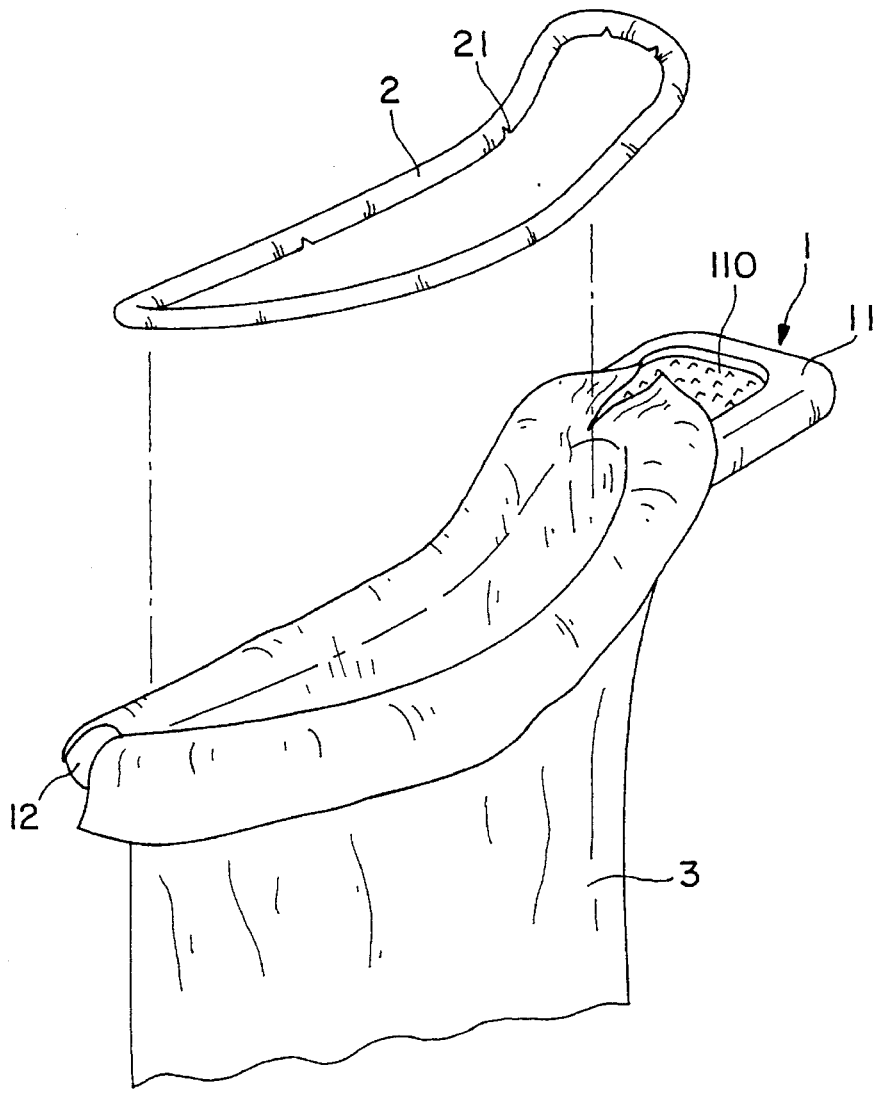
FIG. 4 shows the polybag mounted on the bracket according to the present invention.
Figure 5:
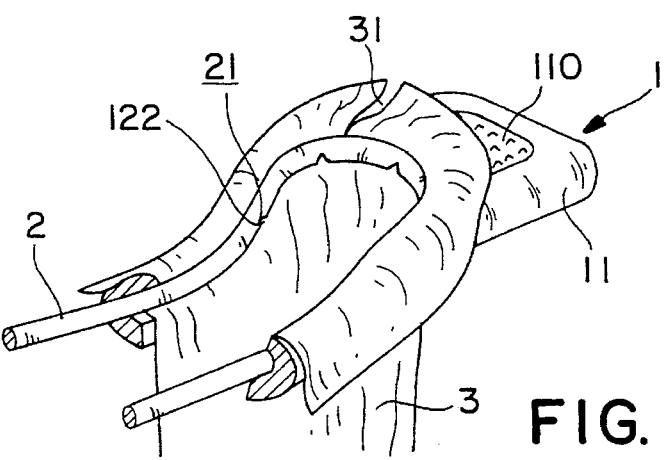
FIG. 5 shows the polybag mounted on the bracket and the packing strip installed.

Referring to FIGS. 4 and 5, the open end of the polybag 3 is inserted through the center opening 120 of the open bearing frame 12 of the bracket 1 from the bottom side, then the border of the orifice of the polybag 3 is turned inside-out (through the splits 31, the border of the orifice of the polybag 3 can be conveniently turned inside-out) and covered over the endless mounting groove 121, then the packing rubber 2 is fitted into the endless mounting groove 121 to fix the polybag 1 in place. When the packing rubber 2 is fitted into the endless mounting groove 121, the triangular blocks 122 pierce the polybag 3 and engage the notches 122 to hold down the polybag 3. Through the flat handle 11, the urine bag can be put around the vulva to collect urine.

It is to be understood that the drawings are designed for purposes of illustration only, and are not intended as a definition of the limits and scope of the invention disclosed.

I claim:

1. A urine collection device for females, comprising: a bracket for carrying a container for collecting urine, said bracket comprising a flat handle at one end, and a bearing frame at an opposite end for fitting around the vulva, said bearing frame comprising a center opening, an endless mounting groove at a top side around said center opening, and a plurality of retaining portions spaced around said endless mounting groove; said container comprising a bag carried on said bracket for collecting urine, said bag having an opening, and a plurality of splits around a border of the opening for permitting the border to be turned inside-out and fastened to the endless mounting groove of said bearing frame; said device further comprising a packing member fitted into the endless mounting groove of said bearing frame to fix said bag in place, said packing member having a plurality of notches which engage with the retaining portions of said bearing frame.

2. The urine collection device of claim 1 wherein said flat handle has two recesses at two opposite sides, each recess having a coarse surface.

3. The urine collection device of claim 1 wherein the retaining portions of said bearing frame are pointed blocks which pierce said bag and engage the notches of said packing member.

* * * * *